US008802370B2

(12) United States Patent
Knapp et al.

(10) Patent No.: US 8,802,370 B2
(45) Date of Patent: Aug. 12, 2014

(54) METHOD AND APPARATUS TO MINIMIZE DIAGNOSTIC AND OTHER ERRORS DUE TO TRANSPOSITION OF BIOLOGICAL SPECIMENS AMONG SUBJECTS

(75) Inventors: Peter M. Knapp, Carmel, IN (US); Travis A. Morgan, Indianapolis, IN (US); Theodore R. Schenberg, Carmel, IN (US)

(73) Assignee: Strand Diagnostics, LLC, Indianapolis, IN (US)

(*) Notice: Subject to any disclaimer, the term of this patent is extended or adjusted under 35 U.S.C. 154(b) by 310 days.

(21) Appl. No.: 12/469,228

(22) Filed: May 20, 2009

(65) Prior Publication Data

US 2009/0291449 A1 Nov. 26, 2009
US 2012/0064515 A2 Mar. 15, 2012

Related U.S. Application Data

(60) Provisional application No. 61/055,628, filed on May 23, 2008.

(51) Int. Cl.
*C12Q 1/68* (2006.01)
*B65D 71/00* (2006.01)
*B01L 9/00* (2006.01)
*A61B 10/00* (2006.01)
*B01L 3/00* (2006.01)

(52) U.S. Cl.
CPC .............. *B01L 9/54* (2013.01); *B01L 2200/16* (2013.01); *B01L 2200/18* (2013.01); *B01L 3/5029* (2013.01); *B01L 2300/021* (2013.01); *A61B 10/0096* (2013.01)
USPC .......................................... 435/6.11; 702/20

(58) Field of Classification Search
USPC ............................................... 435/6; 206/569
See application file for complete search history.

(56) References Cited

U.S. PATENT DOCUMENTS

| 4,122,947 A | 10/1978 | Falla |
| 4,917,867 A | 4/1990 | Jensen |
| 5,783,182 A | 7/1998 | Thompson |
| 6,176,836 B1 | 1/2001 | Trudil et al. |
| 6,251,592 B1 | 6/2001 | Tang et al. |

(Continued)

FOREIGN PATENT DOCUMENTS

WO   WO 2007/035984 A1   4/2007

OTHER PUBLICATIONS

Suba et al. The Journal of Urology, vol. 178, pp. 1245-1248, Oct. 2007.*

(Continued)

*Primary Examiner* — Samuel Woolwine
*Assistant Examiner* — Danna Bicknell
(74) *Attorney, Agent, or Firm* — Woodard, Emhardt, Moriarty, McNett & Henry LLP (57) ABSTRACT

A method and apparatus for minimizing diagnostic errors due to transposition of biological specimens among subjects provides for independent biometric confirmation that a given specimen is from a given donor. In certain embodiments, a biological specimen confirmation kit comprises a portable and openable case housing components of the kit, at least one biological specimen container adapted to receive a biological testing specimen from a donor, and at least one reference sample device adapted to receive a biological reference specimen from the same donor, such that the testing and reference specimens can later be compared for donor match verification by a reference verification entity.

6 Claims, 5 Drawing Sheets

(56) References Cited

U.S. PATENT DOCUMENTS

| 7,264,776 | B2 | 9/2007 | Guo et al. | |
|---|---|---|---|---|
| 2003/0100479 | A1 | 5/2003 | Dow et al. | |
| 2005/0064436 | A1* | 3/2005 | Barrett et al. | 435/6 |
| 2007/0036686 | A1* | 2/2007 | Hatamian et al. | 422/102 |
| 2008/0027756 | A1 | 1/2008 | Gabriel et al. | |

OTHER PUBLICATIONS

Mariappan et al. Identification of mislabeled specimen by molecular methods: case report and review. International J Surgical Pathology 2005;13(3):253-58.*

Demetrick et al. DNA "fingerprint" evaluation of clinical specimen contamination: Application to cytopathology. Pathology Case Reviews 2006;11(2):98-102.*

Huijsmans et al. Single nucleotide polymorphism profiling assay to confirm the identity of human tissues. J Molecular Diagnostics 2007;9(2):205-13.*

Christie et al. A simple and rapid approach to the problem of tissue contamination and patient identity in histopathologic specimens. Human Pathology 2006;37:1536-42.*

Mosse et al. A B-cell lymphoma diagnosed in "floater" tissue: implications of the diagnosis and resolution of a laboratory error. American J of Medical Sciences 2009;338(3):248-51.*

Berg, Karin D. et al., "Floaters in Surgical Pathology Tissues Genetic Identity Testing Potential and Pitfalls", Pathology Case Reviews, vol. 8, No. 3, pp. 103-110, May/Jun. 2003.

Cao, Dengfeng et al., "Little or No Residual Prostate Cancer at Radical Prostatectomy: Vanishing Cancer or Switched Specimen?", Am J Surg Pathol, vol. 29, No. 4, pp. 467-473, Apr. 2005.

International Search Report, PCT/US09/44830, mailed Jul. 27, 2009, 3 pages.

Suba, Eric J. et al., "Patient Identification Error Among Prostate Needle Core Biopsy Specimens—Are We Ready for a DNA Time-Out?", The Journal of Urology, vol. 178, pp. 1245-1248, Oct. 2007.

Trpkov, Kiril et al., "No Residual Cancer on Radical Prostatectomy After Positive 10-Core Biopsy", Arch Pathol Lab Med, vol. 130, pp. 811-816, Jun. 2006.

Written Opinion of the International Searching Authority, PCT/US09/44830, mailed Jul. 28, 2009, 5 pages.

International Preliminary Examination Report for PCT/US2009/44830, Jul. 13, 2011, 15 pgs.

International Supplemental Examination Report for PCT/US2009/44830, Nov. 13, 2012, 7 pgs.

International Preliminary Examination Report for PCT/US2009/44830, 15 pgs, Date of Completion: Jul. 13, 2011.

* cited by examiner

METHOD AND APPARATUS TO MINIMIZE DIAGNOSTIC AND OTHER ERRORS DUE TO TRANSPOSITION OF BIOLOGICAL SPECIMENS AMONG SUBJECTS

CROSS REFERENCE TO RELATED APPLICATIONS

This application claims the benefit of U.S. Provisional Application No. 61/055,628, filed May 23, 2008, which is hereby incorporated by reference.

FIELD OF THE DISCLOSURE

The present disclosure relates generally to the processing of tissue or other biological specimens from subjects, and more particularly to methods and apparatuses to minimize diagnostic and other errors due to transposition of biological specimens among subjects.

BACKGROUND OF THE DISCLOSURE

Several methods are known for administering the collection of biological specimens and processing of same by a laboratory in order to assess the pathology, histology, toxicology, or other important attributes of the specimen of interest, while attempting to maintain the correct association of a given specimen to the donor of that specimen. These methods can include any number of process controls such as unique specimen numbering, clean laboratory technique, standardization of operating procedures, physical segregation, storage, and handling of specimens, and so on. These methods, however, necessarily place a heavy reliance on human handling and compliance, and are therefore susceptible to human error.

It is known, for example, that cases of accidentally switched specimens among cancer biopsy patients may result in misdiagnosis at rates approaching 1% of all cases. The ramifications of such errors are significant in that they can lead to dramatic treatments such as mastectomy or prostatectomy, for example, on patients who do not require these procedures, and conversely the neglected treatment of patients who are unaware of their malignant condition having been incorrectly diagnosed as benign.

A system for minimizing the introduction of human error into the handling and processing of biological specimens, and for providing further an independent means of biometrically confirming that a given specimen is from a given donor is highly desirable.

SUMMARY OF THE DISCLOSURE

In certain embodiments, a donor match verification kit comprises a portable and openable case adapted to house components of the kit, at least one biological specimen container housed within the portable case during transport and storage of the case and removable from the case during use of the container. The biological specimen container is adapted to receive a biological testing specimen from a donor. The kit further includes at least one reference sample device housed within the portable case during transport and storage of the case and removable from the case during use of the device. The reference sample device is adapted to receive a biological reference specimen from the same donor. Each of the case, the container and the device are pre-marked with a donor-unique identifier, the identifier on each of the case, the container and the device being the same.

In certain other embodiments, a method comprises providing a kit as described above, collecting the biological reference specimen from the donor using the reference sample device and forwarding the reference sample device to a reference verification entity. The method further includes collecting the biological testing specimen from the donor, placing the biological testing specimen in the biological specimen container, and returning the biological specimen container to the case.

In yet other embodiments, a method comprises providing a kit as described above, receiving the reference sample device containing the biological reference specimen collected from the donor, receiving at least a portion of the biological testing specimen collected from the donor, and comparing the biological testing specimen to the biological reference specimen to confirm or reject that the biological reference specimen and the biological testing specimen were collected from the same donor.

In even other embodiments, a donor match verification kit comprises a portable and openable case adapted to house components of the kit, the case being divided into at least two separate and non-overlapping compartments, including a procedures compartment and a testing compartment. The procedures compartment includes at least one biological specimen container housed within the portable case during transport and storage of the case and removable from the case during use of the biological specimen container. The biological specimen container is adapted to receive a biological testing specimen from a donor, wherein the biological specimen container is a vial containing an amount of buffered formalin. The procedures compartment further includes at least one buccal swab housed within the portable case during transport and storage of the case and removable from the case during use of the swab, the buccal swab being adapted to receive a biological reference specimen from the donor. The testing compartment includes at least one testing specimen container housed within the portable case during transport and storage of the case and removable from the case during use of the testing specimen container. The testing specimen container is adapted to receive a portion of the biological testing specimen from the donor which has tested positive for a medical occurrence. Additionally, each of the case, the biological specimen container, the swab and the testing specimen container are pre-marked with a donor-unique bar code label, the bar code label on each of the case, the biological specimen container, the swab and the testing specimen container being identical.

DETAILED DESCRIPTION OF THE VARIOUS EMBODIMENTS

For the purposes of promoting an understanding of the principles of the disclosure, reference will now be made to the embodiments illustrated and specific language will be used to describe the same. It will nevertheless be understood that no limitation of the scope of the disclosure is thereby intended, such alterations, modifications, and further applications of the principles of the disclosure being contemplated as would normally occur to one skilled in the art to which the disclosure relates. The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The present disclosure generally provides an apparatus and method for reducing the introduction of human error into the processing and handling of biological specimens, and a virtually fail safe biometric confirmation mechanism to assure specimens are not errantly switched resulting in a particular specimen being associated with an incorrect donor. In certain embodiments, the present disclosure provides a kit containing all of the necessary items applicable to a given biological procedure, with many of the components and the case itself being marked with a donor-unique identifier ensuring that any errant specimen switch may be quickly and easily identified via confirmation that the unique identifiers within a given case match. The kit may also contain a device for the collection of a biological reference specimen from the donor at the same time the specimens for biological testing are obtained, such that the reference specimen can be biometrically matched against the testing specimens from the same patient using a biometric marker that is unique to the donor.

The present disclosure contemplates that the various kit embodiments discussed herein may be provided and used in association with a variety of biological or chemical testing procedures in which it would be desirable to link the testing result with a particular testing subject. For discussion purposes only, the present disclosure discusses the use of the apparatus and method with respect to a biopsy testing procedure. However, it should be appreciated that the kit could be utilized in association with a variety of other procedures, including disease testing, infant confirmation testing, drug testing, blood donation testing, blood transfusion testing, agricultural testing, and meat or other food-origination testing, just to name a few non-limiting examples.

Figure 1:
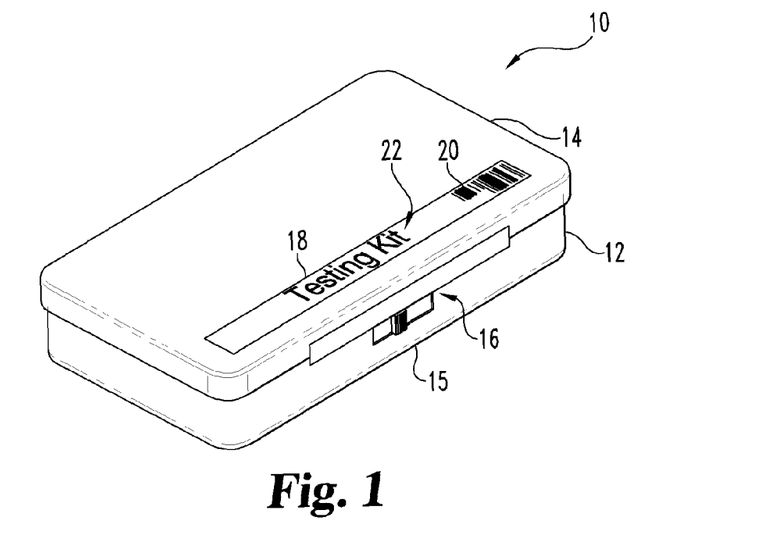
FIG. 1 is a perspective view of a kit, with the case closed, according to an embodiment of the present disclosure.
Figure 2:
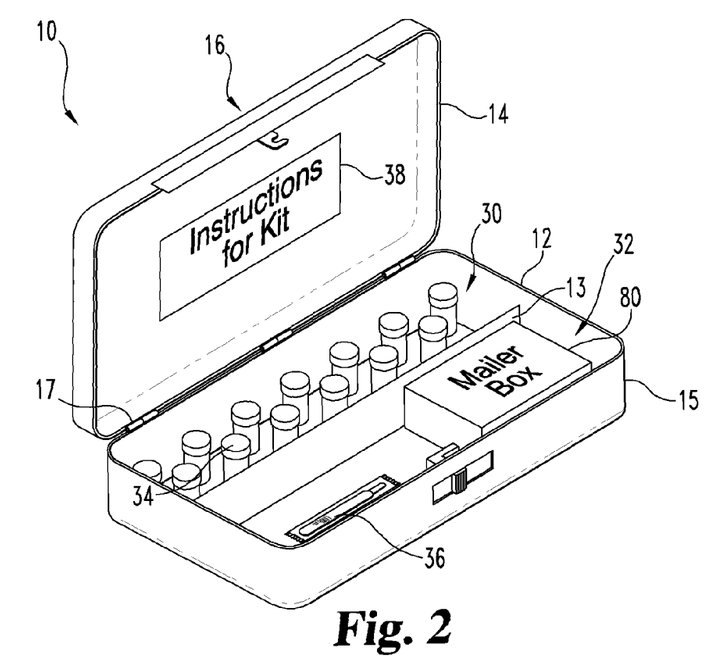
FIG. 2 is a perspective view of a kit, with the case opened, according to an embodiment of the present disclosure.
Figure 3:
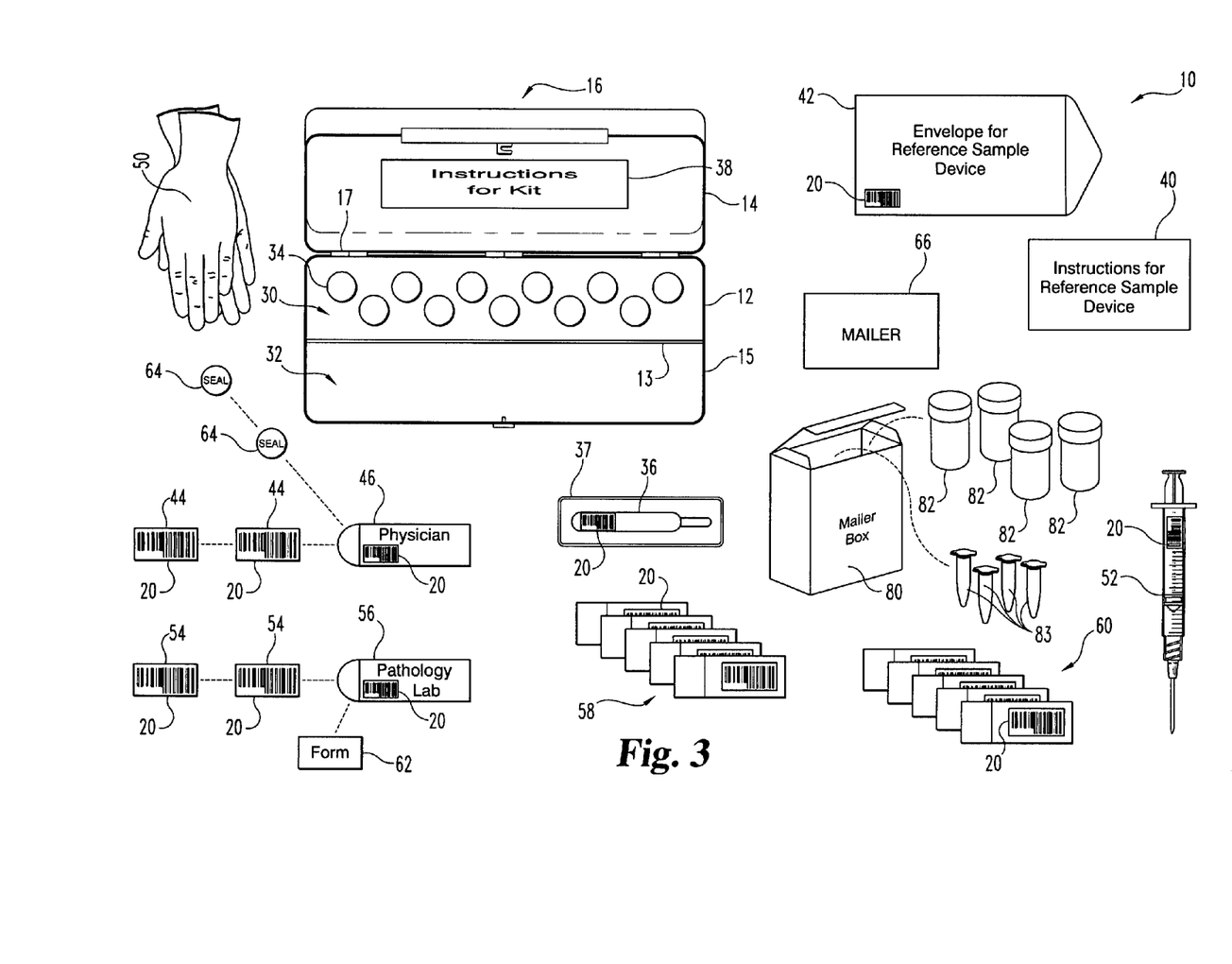
FIG. 3 is a perspective view of a kit, with the case opened and many of the kit components presented for viewing, according to an embodiment of the present disclosure.

Referring now to FIGS. 1-3, there is shown a biological specimen confirmation kit 10 for utilization by one or more medical professionals involved in the implementation of a testing procedure. As mentioned above, for discussion purposes only, the testing procedure discussed herein is a biopsy procedure involving a physician and a pathology lab. The kit 10 includes a case 12 configured to house the components of the kit 10. In certain embodiments, the case 12 is portable and thus can be transported to various locations. In preferred embodiments, the case 12 can be selectively opened (see FIGS. 2 and 3) and closed (see FIG. 1). The case 12 includes a lid 14 selectively openable from a body portion 15 via one or more hinge assemblies 17 (see FIG. 2). It should be appreciated that lid 14 may be engaged with body portion 15 in various other appropriate manners as would occur to one of ordinary skill in the art. Additionally, the lid 14 can be selectively locked to body portion 15 to close the case 12 via latch 16. Latch 16 may be configured as an appropriate selective locking mechanism as would occur to one of ordinary skill in the art. The design and operation of at least latch 16 and hinge assemblies 17 are not critical to the present disclosure. Alternately, latch 16 may be absent. In such alternate embodiments, tamper evidence seals (such as seals 64 discussed below) may be used to prevent and detect tampering with the case 12. A tamper evident seal may be placed along a portion of the engagement between lid 14 and body portion 15 after the case 12 is closed and prior to transport to another entity.

Case 12 may further include an identifying label 18 placed thereon having indicia 22. As examples, indicia 22 could include a designation of the type of kit, the name of the company sponsoring the kit, the name of the company manufacturing the kit, the name of the reference verification entity verifying the donor match, contact information for one or more entities, etc., just to name a few non-limiting examples. Kit 10 may also optionally include instructions 38 detailing the intended and proper use of the kit 10.

In preferred embodiments, many of the components of kit 10 have a donor-unique identifier associated therewith. In particular embodiments, each of the components of kit 10 for which it is desirable to link to a particular donor includes a donor-unique identifier. In the illustrated embodiments, the donor-unique identifier is a bar code 20. Bar code 20 may be human or machine readable. However, it should be appreciated that the donor-unique identifier may be any appropriate identification means as would occur to one of ordinary skill in the art to uniquely identify the item and enable correlation of that item to the donor and to other items identified via the same unique identifier. As non-limiting examples, the donor-unique identifiers may be radio frequency identification tags placed on, embedded in or otherwise associated with the various kit components or uniquely patterned colored tags placed on the various kit components.

In the illustrated embodiment, a bar code 20 is placed or imprinted on label 18 such that the bar code is visible when the case is closed. In other embodiments, the bar code 20 can be placed on case 12 at other appropriate locations such that the bar code is visible when the case is in the closed position. In alternative embodiments, bar code 20 is absent from the case 12.

As illustrated in FIGS. 2 and 3, case 12 can be opened via latch 16 to access the kit components housed within the case. In other embodiments, case 12 may be opened by breaking the tamper evident seal to access the case components. In the illustrated embodiment, case 12 includes upper and lower compartments 30 and 32 defined in body portion 15 by divider 13. However, it should be appreciated that case 12 can be configured and arranged in a variety of other ways as would occur to one of ordinary skill in the art, with the illustrated arrangement being just one example of the numerous possible arrangements. As examples, case 12 could have one single compartment or three or more different compartments for placement of the kit components housed within case 12.

In the illustrated embodiment, upper compartment 30 includes a plurality of biological specimen containers 34 for receiving biological testing specimens. The quantity of containers 34 is not critical to the present disclosure. The container 34 is configured to receive a specimen for biological testing. In the illustrated embodiment, the container 34 is a vial; however, it should be appreciated that the devices for receiving the biological testing specimens may be other appropriate receptacles as would occur to one of ordinary skill in the art, including jars, sleeves, tubes, bottles and flasks, as non-limiting examples. Additionally, each specimen-receiving receptacle, such as vial container 34, preferably includes a bar code 20 placed thereon.

Figure 4:
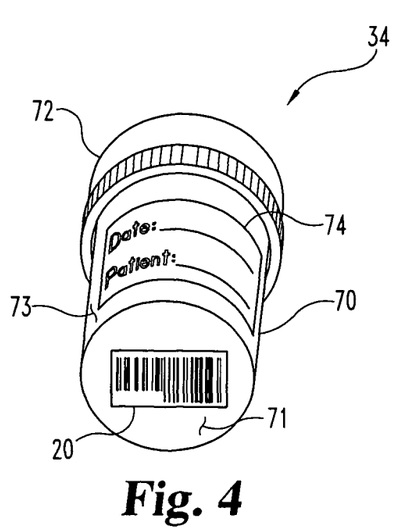
FIG. 4 is a close-up perspective view of a biological specimen container according to an embodiment of the present disclosure.

Turning to FIG. 4, vial container 34 is illustrated in greater detail. As shown, container 34 may include a vial bottle 70 and a removable lid 72 configured to engage the bottle 70 to close the container. The illustrated container 34 includes a bar code 20 placed on bottom surface 71 and an optional label 74 placed on side surface 73 for indicating the patient's name and the date. It is contemplated that the bar code 20 and the optional label 74 may be positioned at other locations on container 34 as would occur to one of ordinary skill in the art. In a particular embodiment in which a biological sample from a particular donor is taken and placed into container 34 for biopsy testing, the container 34 may include an amount of 10% neutral buffered formalin, or another appropriate preservative, therein to act as a preservative and assist in maintaining the integrity of the biological sample for the biopsy procedure.

Referring again to FIGS. 2 and 3, in the illustrated embodiment, lower compartment 32 includes a reference sample device 36 and a plurality of optional kit components, as will be discussed in greater detail below. The reference sample device 36 is configured for the collection of a biological reference specimen from the same donor so that the donor's unique biometric marker may be generated. In the illustrated example, the reference sample device 36 is a buccal swab designed to collect epithelial cells from inside the donor's mouth.

Other appropriate reference specimen collection devices or containers may be included in the kit 10 as would occur to one of ordinary skill in the art. As an example, a reference specimen vial may be included in the kit so that the medical professional may collect a tissue, urine or blood sample, as examples, and place the sample in the vial to be used as a reference specimen. It should be appreciated that the reference specimen collection device may be any appropriate device configured to receive any appropriate biological reference sample from the donor as would occur to one of ordinary skill in the art. It is contemplated that the biological reference sample may be one from which a unique biometric marker, such as DNA profile, may be generated. However, it should be appreciated that the present disclosure contemplates other possible reference means other than DNA, including an antibody profile, as one non-limiting example.

In addition to containers 34 and reference sample device 36, FIG. 3 illustrates a plurality of kit components which may optionally be included in kit 10. In the particular example situation involving a biopsy procedure, it is contemplated that the kit 10 and its contents may be initially handled by a physician responsible for collecting the biological testing specimen as well as the reference specimen, and then transferred to a pathology lab responsible for conducting the biopsy testing on the biological testing specimen collected from the donor. As such, many of the components are designated for use as by the physician or the pathology lab in relation to the specific example of the biopsy testing procedure. As stated above, it should be appreciated that the kit 10 may be used in association with a variety of other procedures and also may be used by a variety of other medical professionals. FIG. 3 illustrates many of the components removed from case 12 so that the components may be easily presented for display. Additionally, it is contemplated that some or all of the displayed components in FIG. 3 may be housed in the lower compartment 32 of the case. However, it should be appreciated that the components of kit 10 can be otherwise arranged within case 12 as would occur to one of ordinary skill in the art.

As illustrated, reference sample device 36 may include a bar code 20 thereon and may optionally be provided in a clear plastic sleeve 37. Kit 10 may optionally include instructions 40 detailing the intended and proper use of the device 36. Additionally, kit 10 may optionally include an envelope 42, having bar code 20 optionally placed thereon, for return of the device 36 to a reference verification entity by either the physician or the pathology lab after the reference sample has been collected from the donor so that a donor-unique biometric profile may be generated. It should be appreciated that the reference verification entity may be an independent third party, independent from the physician and pathology lab discussed herein. In lieu of an envelope 42, kit 10 may optionally include a bar coded mailing label for return of the device 36 to the reference verification entity. Additionally, kit 10 may optionally include a needle syringe 52 to use in the collection of the biological testing specimen and/or the biological reference specimen from the donor, with the syringe 52 optionally including a bar code 20 thereon. Kit 10 may also optionally include one or more latex gloves 50 for use by a medical professional during the testing procedure. In other embodiments, the gloves 50 and/or the syringe 52 may be absent.

Kit 10 may also include one or more labels 44, each having a bar code 20 imprinted thereon, for placement on documents including paperwork in the donor's particular medical file under the control of the physician. The labels 44 may optionally be housed in an envelope 46 designated for the physician also having a bar code 20 thereon. Similarly, kit 10 may include one or more labels 54, each having a bar code 20 imprinted thereon, for placement on things required by the pathology lab, including documents such as paperwork in the donor's particular medical file or microscope slides to track testing specimens, to name a few non-limiting examples. The labels 54 may optionally be housed in an envelope 56 designated for the pathology lab and also having a bar code 20 thereon. It is also contemplated that other items designed for the physician and/or pathology lab may be included in the envelopes 46 and/or 56, or included separately in the kit 10, including instructions and authorization documentation as examples.

As mentioned above, in certain embodiments, kit 10 may optionally include one or more tamper evident seals 64 to be placed on items in which it is desirable to prevent and detect tampering. The seals 64 may optionally be housed in the physician's envelope 46. In the illustrated embodiments, two seals 64 are provided in the kit 10. One of the seals 64 may be used to seal the envelope 42 after the reference sample device 36 has acquired the biological reference specimen and been placed in the envelope. The other of the seals 64 may be placed on the case 12 by the physician (or physician's staff) following the collection of the biological reference specimen and the biological testing specimen, and prior to transporting the case to a testing entity such as a pathology lab. Additional tamper evidence seals may be provided for additional events, including placement on the case 12 following the completion of the particular testing procedure by a testing entity and prior to transporting the case to a reference verification entity for donor match verification. The seal 64 may be placed on the outside of case 12 at a variety of locations along the engagement of lid 14 to body portion 15 so that if an unauthorized individual attempted to open (or successfully opened) the lid 14 to access the kit components housed within the case, the integrity of seal 64 would be compromised and the unauthorized activity would be evident by viewing the seal.

Additionally, kit may also optionally include a donor match verification request form 62 to be completed by the pathology lab upon determining a positive test result for a particular donor. The form 62 may optionally be housed in the pathology lab envelope 56.

Kit 10 may include a variety of appropriate mechanisms for receiving a portion of the biological testing specimen and forwarding the specimen to the reference verification entity. The specimen is forwarded to the reference verification entity for comparison with the biological reference specimen to confirm a matching donor. In certain embodiments, it is contemplated that a portion of the biological testing specimen may be forwarded to the reference verification entity following a positive result from the testing procedure. Regarding the specific vehicle used to transport the specimen, as one non-limiting example, a portion of the positive-testing specimen may be placed in one or more containers which are transported to the reference verification entity. As another non-limiting example, a portion of the positive-testing specimen may be placed one or more slides which are transported to the reference verification entity. It should be appreciated that the device used to forward a portion or all of the biological reference specimen to the reference verification entity may be other appropriate devices as would occur to one of ordinary skill in the art.

In certain embodiments, kit 10 may optionally include one or more microscope slides 58 having bar code 20 optionally placed thereon. In this way, the pathology lab personnel may place a portion of the biological testing specimen on the one or more microscope slides 58 and transfer the slides to the reference verification entity. In other embodiments, slides 58 are absent from the kit 10 and the pathology lab may provide the microscope slides, or other appropriate device, to transport a portion of the positive-testing biological specimen.

Kit 10 may also optionally include a plurality of containers 82 sized and configured to be received in a transport box 80. Containers 82 may be configured and adapted to receive one or more microscope slides, such as slides 58, containing a portion of the biological testing specimen. Transport box 80 and containers 82 may each contain a donor-unique identifier, such as bar code 20, imprinted thereon. In certain embodiments, upon determining a positive test result, pathology lab personnel will place at least a portion of the biological testing specimen on one or more microscope slides and place the slides in containers 82 for transport to the reference verification entity. The containers 82 may be configured in a variety of ways such that at least one microscope slide may be received in each container. In the illustrated embodiment, each container 82 may receive up to four microscope slides and up to four containers 82 may be housed within the transport box 80. However, it should be appreciated that the arrangement and number of containers 82 and transport box 80 can be varied as would occur to one of ordinary skill in the art. In some embodiments, the microscope slides may be placed in the containers 82, the containers 82 may be placed in the transport box 80, and the transport box 80 may be placed in the illustrated mailing envelope 66 for transport to the reference verification entity. In other embodiments, the transport box 80 may be transported to the reference verification entity without placement in a mailing envelope or other type of packaging.

In other embodiments, slides 58 and containers 82 may be absent from the kit 10 and in lieu thereof, kit 10 may optionally include a plurality of containers 83 sized and configured to be received in the transport box 80. Containers 83 may be configured and adapted to directly receive a portion of the biological testing specimen therein. Containers 83 may contain donor-unique identifiers, such as bar codes 20, imprinted thereon. Containers 83 may be uses as a vehicle for transporting the positive-testing biological reference specimen to the reference verification entity in the same or similar manner as discussed above with respect to containers 82. Additionally, it should be appreciated that the containers 83 may be configured differently than as illustrated as would occur to one of ordinary skill in the art.

In the specific example of a biopsy procedure, it is contemplated that the pathology lab will typically receive the biological testing specimens which have been placed in the one or more containers 34. To perform biopsy testing, the specimens may be processed by the pathology lab personnel in the ordinary manner, typically including placement of the specimens into paraffin blocks from which microscope slides are made for inspection by a pathologist. As illustrated in FIG. 3, a plurality of slides 60 pre-labeled with bar codes 20 may also optionally be included in the kit 10 for use by the pathology lab. In other embodiments, the slides 60 are absent from kit 10 and the pathology lab personnel may place labels 54 on microscope slides provided by the pathology lab. Regardless of how the slides are provided, placement of the donor-unique identifiers on the microscope slides (and also optionally the paraffin blocks) used by the pathology lab helps to ensure a continued link between the biological testing specimen and the donor-unique identifier throughout the testing procedure.

Figure 5:
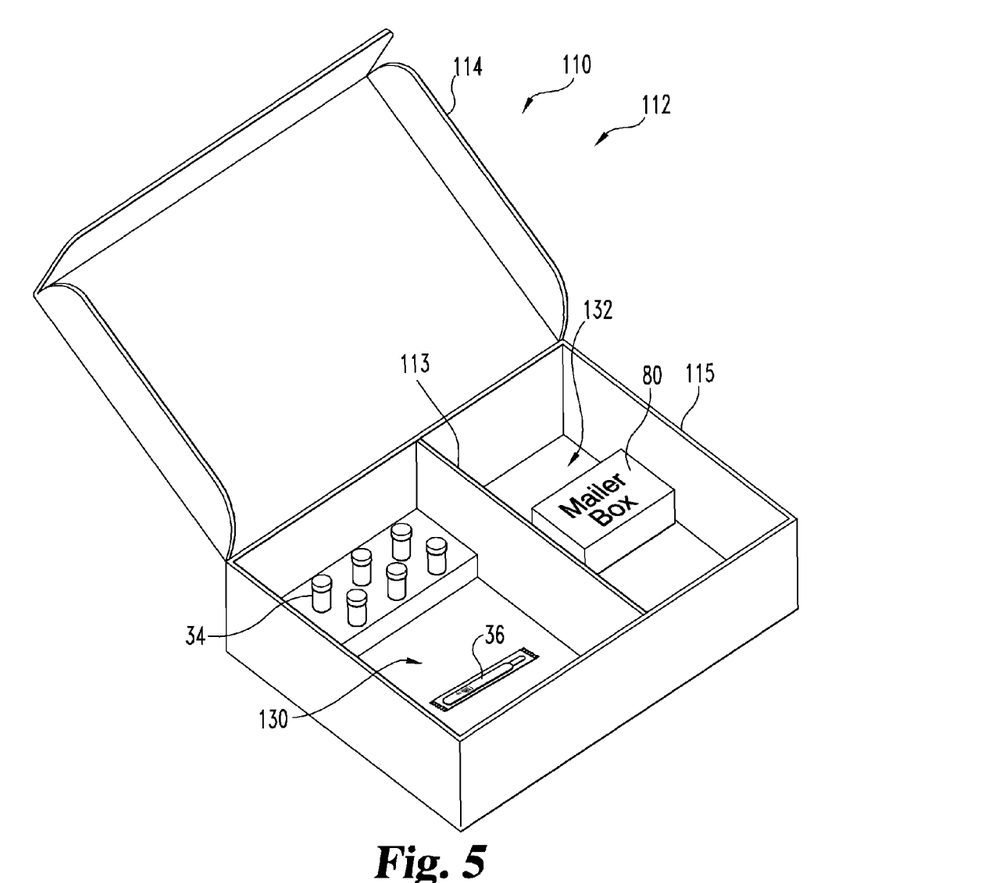
FIG. 5 is a perspective view of a kit, with the case opened, according to another embodiment of the present disclosure.

FIG. 5 illustrates another example case as part of a kit according to another embodiment of the present disclosure. In the illustrated embodiment, kit 110 having case 112 includes many, if not all, of the same contents as kit 12 and is simply serving to illustrate another example configuration of the case which may be used in accordance with the present disclosure. Additionally, many of the components discussed above will not be illustrated or discussed with respect to kit 110 for the sake of brevity, however it should be appreciated that many, if not all, of the same components may be included in kit 110.

As illustrated, kit 110 includes a body portion 115 and a lid 114 selectively engagable with the body portion 115. In certain embodiments, the body portion and lid may be integral portions of the case, with the lid being movable with respect to the body portion to selectively close the case. The case 112 may be composed of a variety of appropriate materials, including plastic or paper-based materials as examples. As illustrated, case 112 is preferably divided into separate, discrete and non-overlapping portions, segments or compartments, including the procedures compartment 130 and the pathology lab compartment 132 with divider 113 separating the compartments. In the particular illustrated embodiment, containers 34 and swab 36 are provided in compartment 130, as those compartments are accessed by a physician or physician's office employee as will be discussed in greater detail below. Additionally, in the particular illustrated embodiment, the mailer box 80 (along with the particular vehicle provided to transport the positive-testing biological specimen to the reference verification entity) are provided in compartment 132. In this way, only the components to be accessed by the physician or physician's office employee are provided in compartment 130, separate from the components to be accessed by the pathology lab provided in compartment 132. In certain embodiments, one or both of the compartments may include an appropriate lid or cover which can be selectively positioned over the component. It should be appreciated that the case having the separate and divided compartments can be configured differently as would occur to one of ordinary skill in the art.

Figure 6:
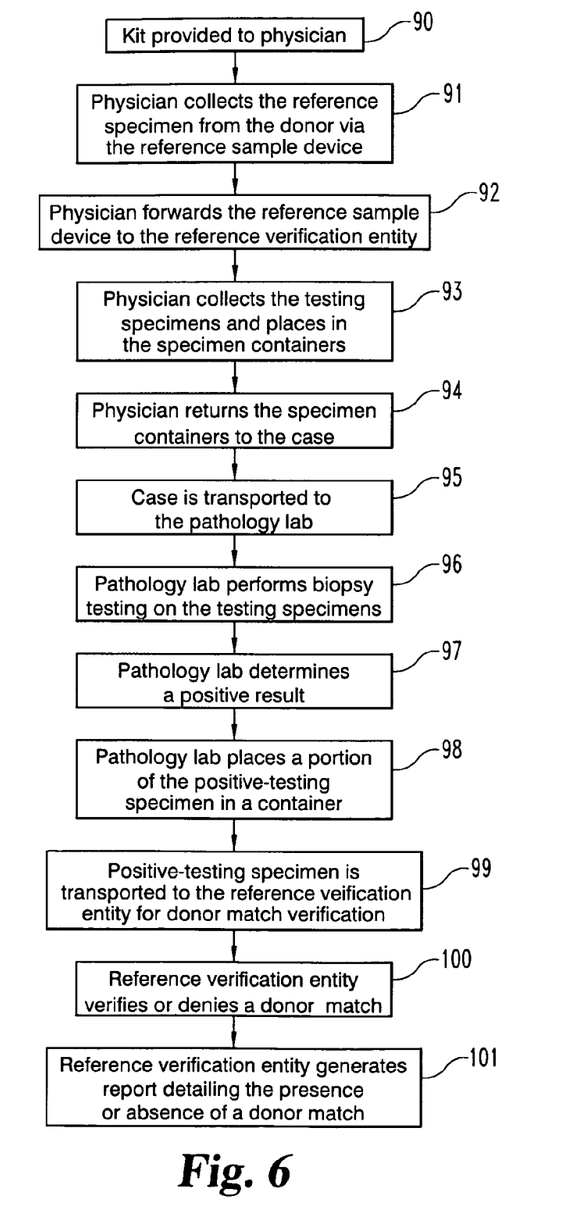
FIG. 6 is a flow chart of steps according to an embodiment of the present disclosure.

The various procedures contemplated by the present disclosure will generally be discussed with reference to the flow chart of FIG. 6. As mentioned above, a biopsy procedure involving a pathology lab operable to conduct biopsy testing will be used as an example for discussion purposes only. It should be appreciated that a variety of other testing procedures can be executed using the kit of the present disclosure where it is desirable to ensure the identity of a donor. Additionally, with respect to the flow chart of FIG. 6, for simplicity the steps may refer to the "physician" or the "pathology lab";

however, it should be appreciated that such terms are meant to include a variety of healthcare professionals, including nurses, surgical assistants, administrative personnel, office assistants, lab technicians, etc. Further, the various procedures will be discussed with respect to kit 10 and case 12 for simplicity, however it should be appreciated that kit 110 and case 112 may also be used in accordance with the various procedures discussed.

In use, at step 90 the kit 10 is supplied to a physician performing the specimen collection for the biopsy procedure. If applicable, the tamper evident seal on the outside of the case is observed to assure that the case 12 has not been opened prior to receipt by the physician. In certain embodiments, it may be desirable to open the kit 10 within the particular procedure room shortly prior to performing the biopsy procedure. Optionally, labels 44 may be removed from envelope 46 and affixed to the donor's paperwork at the physician's office thereby linking from that point forward the donor-unique identifier via bar code 20 with the specific donor undergoing the biopsy procedure.

At step 91, the physician collects the biological reference specimen via the reference sample device 36. If optional outer protective covering 37 is present, the physician must first remove the device 36 from the covering 37. As illustrated, the device 36 may be a buccal swab designed to collect cells from inside the donor's mouth area. After the reference specimen is collected, the device 36 may optionally be placed in the bar coded protective storage envelope 42 and the envelope 42 may be sealed with one of the tamper evident seals 64. At this point, the envelope 42 containing the device 36 may be mailed to the reference verification entity at step 92 or may be placed back into case 12 at step 92 for transport to the pathology lab and then later transport on to the reference verification entity.

At step 93, the physician collects the biological testing specimens via a needle biopsy procedure, as one non-limiting example, and places the specimens in the containers 34. In certain embodiments, any unused containers 34 may be removed from case 12 and discarded. The physician then returns the containers 34 containing biological testing specimens to the case 12 at step 94 and closes the case. Optionally, the physician may remove the other tamper evident seal 64 from the case 12 prior to closing the case and place the seal 64 on the outside of the closed case along the engagement of lid 14 to body portion 15. In certain embodiments, the seal 64 may be placed over the engagement between lid 14 and body portion 15. The case 12 housing the containers 34 containing biological testing specimens, in certain embodiments the reference sample device 36, and any remaining kit components is then transported to a pathology lab at step 95 to conduct biopsy testing on the testing specimens collected from the donor.

Upon receipt at the pathology lab, if applicable the tamper evident seal is observed to assure that the case 12 has not been opened since leaving the possession of the physician. In certain embodiments, the pathology lab visually or by use of computer scanning equipment confirms that all components having the donor-unique identifier (in the illustrated embodiment, bar code 20) in the case 12 of the kit 10 match to confirm that the identified donor is linked to the components of the kit.

If the reference specimen device 36 was not previously transferred to the reference verification entity by the physician and was placed in the case 12, in certain embodiments the device 36 (optionally sealed in an envelope) may be removed from the case 12 by the pathology lab and sent to the reference verification entity. The reference verification entity may generate the donor's unique biometric profile, such as a DNA profile, and store the profile in a database associated with the donor-unique identifier (in the illustrated embodiment, bar code 20) on the device 36 and/or the envelope 42 containing the device.

At step 96, the pathology lab performs biopsy testing on the specimens. The biological testing specimens in the containers 34 may be processed by the pathology lab in a variety of possible manners, an example including placement of the specimens into paraffin blocks from which microscope slides are made for inspection by a pathologist. In some embodiments, kit 10 may include a plurality of slides 60 pre-marked with the donor-unique identifier upon which the pathologist may place the processed specimens for inspection. In certain embodiments, labels 54 may be removed from envelope 56 and affixed to a variety of possible items, including documents associated with the particular donor, microscope slides provided by the pathology lab, and/or paraffin blocks to ensure a continued link between the specimens and the donor-unique identifier.

If the pathology lab determines a positive result during testing of the specimens at step 97, including as an example the presence of cancerous cells in one or more of the specimens, all or a portion of the positive-testing specimen is transferred to the reference verification entity to verify a donor match between the positive-testing specimen and the reference specimen initially collected from the donor. In some embodiments, the pathology lab my place a portion of the positive-testing specimen into one or more containers 83 at step 98 which are to be transferred to the reference verification entity. In certain other embodiments, the pathology lab may place a portion of the positive-testing specimen onto one or more microscope slides 58 which are to be transferred to the reference verification entity. In other embodiments, the pathology lab may simply transfer the one or more slides 60 having positive-testing specimens thereon to the reference verification entity. In yet other embodiments, the positive-testing specimens may be transferred to the reference verification entity on one or more slides provided by the pathology lab and marked with labels 54 having donor-unique identifiers imprinted thereon. Additionally, the pathology lab may complete the donor match verification request form 62, if present in kit 10, and transport the completed form 62 to the reference verification entity along with the positive-testing specimens.

The positive-testing specimens may be transferred to the reference verification entity for donor match verification at step 99 in a variety of possible manners. In certain embodiments, the containers or slides having the positive-testing specimens may be placed in transport box 80. In such embodiments, the slides may first be placed in slide containers 82 which are placed in transport box 80. Transport box 80 may be placed in mailing envelope 66, optionally containing the donor-unique identifier, and mailed to the reference verification entity. In other embodiments, the containers or slides having the positive-testing specimens may be placed back in case 12 (optionally via transport box 80) and the case 12 may be closed, sealed, and transported to the reference verification entity. In certain embodiments in which the reference sample device 36 has not yet been transferred to the reference verification entity, the device 36 is transported to the reference verification entity along with the positive-testing specimens.

Upon receipt of the reference sample device 36 (at whichever point in the sequence of events contemplated by the present disclosure), the reference verification entity generates a donor-unique biometric profile, such as a DNA profile as one non-limiting example, and associates that profile with the donor-unique identifier placed on at least the device 36. Upon receipt of the positive-testing specimens, the reference verification entity generates a donor-unique biometric profile, such as a DNA profile as one non-limiting example, and associates that profile with the donor-unique identifier placed on at least the microscope slides containing the positive-testing specimens. At step 100, the reference verification entity then verifies or denies a donor match between the reference specimen and the positive-testing specimens. Optionally, at step 101 the reference verification entity may generate a report detailing the presence or absence of a donor match between specimens and transmit the report to the pathology lab and/or the physician. If the donor match is positive, the report will confirm that the biological specimen from which the diagnosis was obtained by the pathology lab matches the donor from which the reference specimen was initially collected. If the donor match is negative, the report will inform the medical professional that the biological specimen from which the diagnosis was obtained by the pathology lab does not match the donor from which the reference specimen was initially collected.

In the event of the absence of a donor match, the reference verification entity may compare the donor-unique biometric profile from the non-matching positive-testing specimen against the reference verification entity's database of profiles in an attempt to identify the donor from which the positive-testing specimens were obtained. In this way, it may be possible to avoid reporting a false negative result to that particular donor (or correct a previous false negative report). Additionally, after the passage of a certain amount of time, the reference verification lab may optionally generate a report to the pathology lab and/or the physician for each reference specimen from which a donor-unique biometric profile was generated and where no matching profile was observed from any of the positive-testing specimens received by the reference verification entity (an "unmatched reference specimen"), indicating by default that the pathology lab did not determine a positive result from the donor's specimens and there is no indication that a false positive has potentially been reported for this donor.

In the event that a particular donor undergoes a surgical procedure to have the positive-testing material removed from the body subsequent the procedures above, a portion of the removed material may be transferred to the reference verification entity so that a donor-unique biometric profile may be generated from the gross specimen removed from the donor. The reference entity lab may then compare the profile generated from the gross specimen removed from the donor with the profiles obtained from the positive-testing specimens received from the pathology lab and/or the reference specimen to provide additional assurance of a match between the donor and a positive diagnosis.

The kit 10 and methods contemplated by the present disclosure reduce the possibility for human error due to the donor-unique identifying of many components in the kit 10 in a highly process-controlled setting removed and independent from the medical office and prepared prior to collection, rather than relying on healthcare providers to manually identify and segregate specimens at the time of specimen collection. The kit 10 and methods contemplated by the present disclosure also reduce the time demands on healthcare providers because many of the contents of kit 10 are uniquely identified in advance of a procedure, and because record keeping can be streamlined using computerized rather than manual specimen tracking methods through the use of computer-readable donor-unique identifiers, such as bar codes as one non-limiting example. Additionally, the kit 10 and methods contemplated by the present disclosure allow for a specimen switch to be readily identified by manual or computerized comparison of the donor-unique identifiers to the corresponding donor paperwork. Further, in the unlikely event that a specimen switch occurs and is not observed by comparison of the donor-unique identifiers against the donor paperwork, the switch will be detected by virtue of the independent biometric matching of the specimen against the donor reference specimen obtained at the time of original specimen collection.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected. This application is intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method, comprising:
   providing a donor match verification kit to a physician at a collections site, the kit including:
   (1) a portable and openable case adapted to house components of the kit;
   (2) at least one reference sample device housed within the portable case during transport and storage of the case, removable from the case during use of the device, and adapted for receiving a biological reference specimen to be collected from a donor at the collections site, wherein the reference sample device is a buccal swab; and
   (3) at least one biological specimen container housed within the portable case during transport and storage of the case, removable from the case during use of the container, and adapted for receiving a biological testing specimen to be collected from a donor at the collections site, wherein the reference sample device is discrete and detached from the biological specimen container, and wherein each of the case, the reference sample device and the biological specimen container are pre-marked with a same donor-unique identifier, wherein the donor-unique identifier is a bar code;
   receiving the reference sample device from the collections site, wherein the reference sample device is received at a verification site, the reference sample device containing the biological reference specimen collected from the donor at the collections site during a physician office visit;
   receiving at least a portion of the biological testing specimen from a testing site different from the collections site, wherein the at least a portion of the biological testing specimen is received at the verification site, wherein the biological testing specimen is a surgical biopsy tissue specimen that was collected from the donor at the collections site during the same physician office visit in which the biological reference specimen was collected, and wherein the biological testing specimen was tested positive for cancer as part of biopsy testing at the testing site;
   generating a donor-unique DNA profile from the biological reference specimen at the verification site;
   generating a donor-unique DNA profile from the at least a portion of the biological testing specimen at the verification site; and comparing the donor-unique DNA profile of the at least a portion of the biological testing specimen to the donor-unique DNA profile of the biological reference specimen to confirm or reject that the biological reference specimen and the biological testing specimen were collected from the same donor, wherein the comparing occurs at a the verification site, which is independent of the collections site and the testing site.

2. The method of claim 1, wherein the kit further comprises an envelope adapted for housing the reference sample device for transport.

3. The method of claim 1, further comprising generating a report identifying the confirmation or rejection at the verification site.

4. The method of claim 1, wherein the biological specimen container is a vial containing an amount of buffered formalin.

5. The method of claim 1, wherein each of the case, the biological specimen container and the reference sample device includes a tamper-evident security seal placed thereon to detect tampering.

6. The method of claim 1, further comprising comparing the donor-unique identifier of the reference sample device to the donor-unique identifier of the biological specimen container to confirm or reject that the biological reference and testing specimens were collected from the same donor, wherein the comparing the donor-unique identifiers occurs at the verification site.

* * * * *